United States Patent [19]

Perry et al.

[11] 4,345,459
[45] Aug. 24, 1982

[54] SENSING DEVICE

[75] Inventors: Ralph A. Perry; James M. Booe, both of Indianapolis, Ind.

[73] Assignee: Emhart Industries, Inc., Indianapolis, Ind.

[21] Appl. No.: 198,058

[22] Filed: Oct. 17, 1980

[51] Int. Cl.³ .............................................. G01N 25/18
[52] U.S. Cl. ................................................. 73/61.1 R
[58] Field of Search .............. 73/61.1 R, 53; 340/603, 340/618

[56] References Cited

U.S. PATENT DOCUMENTS

| | | | |
|---|---|---|---|
| 3,720,797 | 3/1973 | Gunn et al. | 73/61.1 R X |
| 3,918,034 | 11/1975 | Orth, Jr. | 73/448 X |
| 3,946,625 | 3/1976 | Miyazaki et al. | 73/61.1 R |
| 4,116,045 | 9/1978 | Potter | 73/61.1 R |
| 4,131,773 | 12/1978 | Maham et al. | 73/61.1 R X |
| 4,221,125 | 9/1980 | Oliver et al. | 73/61.1 R |
| 4,223,552 | 9/1980 | Goldstein | 73/61.1 R |

FOREIGN PATENT DOCUMENTS

| | | |
|---|---|---|
| 2601410 | 7/1977 | Fed. Rep. of Germany ... 73/61.1 R |
| 2837920 | 3/1980 | Fed. Rep. of Germany ... 73/61.1 R |
| 52-17891 | 2/1977 | Japan ............................... 73/61.1 R |

Primary Examiner—Anthony V. Ciarlante
Assistant Examiner—Joseph W. Roskos
Attorney, Agent, or Firm—Robert F. Meyer; David W. Gomes

[57] ABSTRACT

A device for sensing a substance on the surface of a liquid of the type including a float and a sensing element mounted on the float for extending into the liquid, includes a plastic encasement enclosing all portions of the element to be exposed to the liquid for preventing interference with the operation of the element by substances in the liquid other than the substance to be sensed.

5 Claims, 7 Drawing Figures

SENSING DEVICE

BACKGROUND OF THE INVENTION

1. Field of the Invention

The present invention generally relates to sensing devices and, in particular, to such devices which use a floatation means for supporting a sensing element in proximity to the surface of a liquid.

2. Statement of the Prior Art

Sensing devices are often required to operate in hazardous environments. One very common hazardous environment for a wide variety of sensors is that of exposure to chemical agents which may either be corrosive in nature or be of a type which otherwise inteferes with the normal operation of the sensing device. One such hazardous environment which has been found to exist is in the area of detecting hydrocarbon containing substances in ground water. It has been found that various chemical compositions present in ground water from both natural and man made sources are corrosive or otherwise interfere with the sensing elements employed. To insure the long term reliability of the operation of such sensing elements, it is necessary to avoid the disadvantageous effects on the sensors used of the chemical compositions present in ground water.

SUMMARY OF THE INVENTION

Accordingly, a sensor used for detecting hydrocarbon containing substances present in ground water has been improved to avoid the disadvantageous effects of exposure to the various chemical substances contained in ground water. The improvement is in a device for sensing a substance on the surface of a liquid of the type including a floatation means and a sensing element mounted on the floatation means for extending into the liquid, wherein the improvement comprises a plastic encasement enclosing all portions of the sensing element to be exposed on the liquid for preventing interference with the operation of the element by substances on the liquid. In one embodiment, the sensing element includes an axially leaded semiconductor junction device and the encasement includes shrink tubing having a wall thickness of approximately 0.015 inches or less. In this embodiment, epoxy resin is used to seal the ends of the shrink tubing to the floatation means to insure isolation of the sensing element.

BRIEF DESCRIPTION OF THE DRAWINGS

The present invention is illustratively described with respect to the appended drawings in which.

DETAILED DESCRIPTION OF THE DRAWINGS

Figure 1:
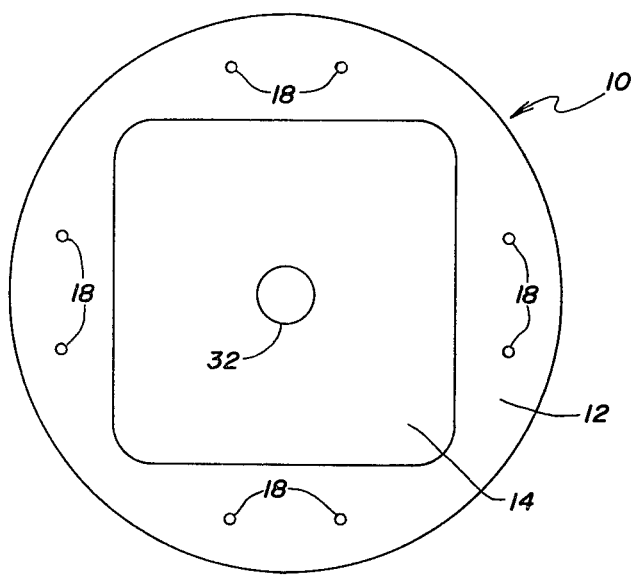
FIG. 1 is a bottom view of a sensing device member constructed according to one embodiment of the present invention.
Figure 2:
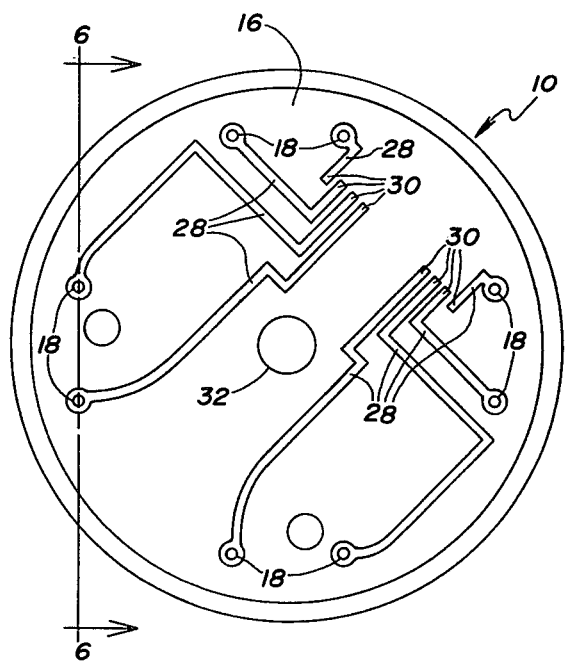
FIG. 2 is a top view of the member of FIG. 1.
Figure 3:
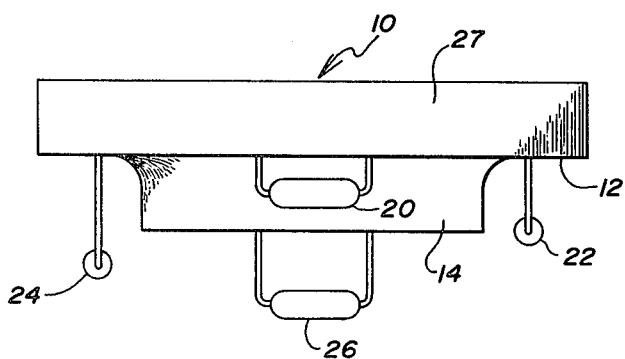
FIG. 3 is a side view of the member of FIGS. 1 and 2 further including a plurality of sensing elements.

In respect to FIGS. 1, 2 and 3, member 10 of a sensing device is shown with bottom, top and side views, respectively. The member 10 generally includes a mounting surface 12, a floatation means 14, and a top surface 16. The downwardly facing mounting surface 12 includes a plurality of apertures 18 in which sensing elements may be mounted. The apertures 18 are arranged in pairs to allow use of dual leaded sensing elements. The sensing elements 20, 22, 24 and 26 are shown in FIG. 3 extending from the apertures 18 to various distances from the downwardly facing surface 12. The sensing elements 20, 22, 24 and 26 are dual leaded semiconductor junction devices or diodes. The upper ends of the apertures 18 are shown extending to the upper surface 16 in FIG. 2.

The floatation means 14 extends downwardly from the mounting surface 12 and is intended to exhibit a positive bouyancy in whatever medium is chosen for the sensor to operate. The size of the floatation means 14 is designed to cause the mounting surface 12 to be located at the surface of the liquid in which the device is operating. By these means, the sensing elements, which are located at predetermined distances from mounting surface 12, are held at known distances below the liquid surface. This allows accurate measurements to be taken of the depth of the substances located on top of the liquid medium.

The entire sensing device member 10 including the floatation means 14 and an upper section 26 forming the mounting surface 12 and the upper surface 16 is made from a closed cell foamed neoprene rubber generically known as nitrile and available under the tradename NITROPHYL from Rogers Corporation of Willimantic, Connecticut. The material nitrile is useful in the applications of the present invention because it exhibits resistance to chemical decomposition when exposed to a variety of substances including hydrocarbons. Thus, when used to detect the presence of hydrocarbons on the surface of ground water, the nitrile does not decompose when exposed to either ground minerals or the hydrocarbon substances.

The top surface 16 is used for connecting the sensing elements 20, 22, 24 and 26 to an electrical cable for eventual connection to a sensing or measurement instrument (not shown). The top view of the sensing device member 10 shows a plurality of printed circuit lands deposited on the top surface 16, which lands 28 each has one end thereof located in proximity to each of the apertures 18. These ends are so located to allow connection of the sensing elements thereto by such means as soldering. The lands 28 each have another end 30, all of which are proximally located to allow connection thereof to a multiconductor cable. The lands 28 are directly deposited on the surface of the nitrile to avoid the use of a separate printed circuit board in addition to the construction of the member 10. The process by which the printed circuit lands are so formed on the surface of nitrile is covered by one or more of U.S. Pat. Nos. 3,956,041; 4,160,050; 4,144,118, which patents are assigned to the Kollmorgen Corporation. The application of the printed circuit lands 28 to the nitrile was performed for the present embodiment by PCK Technology of Glen Cove, New York.

As shown in FIGS. 1 and 2, a central aperture 32 is located through the middle of the member 10 for allowing slidable mounting of the member 10 on a vertical member facilitating the ability of the member 10 to follow the level of the liquid or water being monitored.

Figure 4:
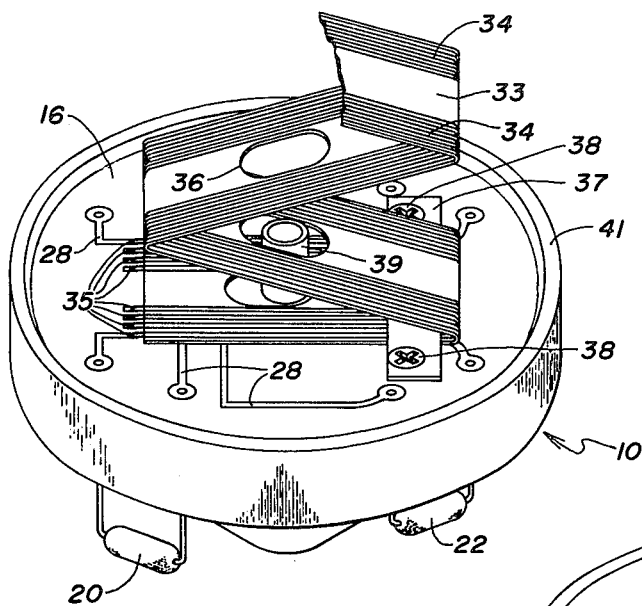
FIG. 4 is a perspective view of the member as shown in FIG. 2 including electrical conductors connected thereto.

FIG. 4 shows the sensing device 10 having an electrical conductor in the form of a ribbon cable 33 connected to the lands 28. The cable 33 used for the present embodiment is available from Amp Incorporated under part No. 5107-1202-2. The cable includes eight separate conductors 34 located along the edges of the cable 33 in pairs of four. Each of the conductors 34 has a terminal 35 connected to the end thereof which terminals 35 are soldered to the separate lands 28 at their ends 30. The cable 33 is modified by the inclusion of a series of holes 36 located approximately midway between the folds of the cable. In the present embodiment, a guide cable (not shown) passes through the holes 36. During construction, the cable is initially held to the top surface of the device 10 by means of a stran relief bar 37 which is secured by a pair of screws 38 to the top surface 16 of the device 10. FIG. 4 further shows a guide pipe means 39 which is secured within the aperture 32 of FIG. 2. In operation, a guide cable is located through the holes 36 and the guide pipe 39 to stabilize the sensing device from lateral movement but to allow vertical movement in accordance with changes in water level.

Figure 5:
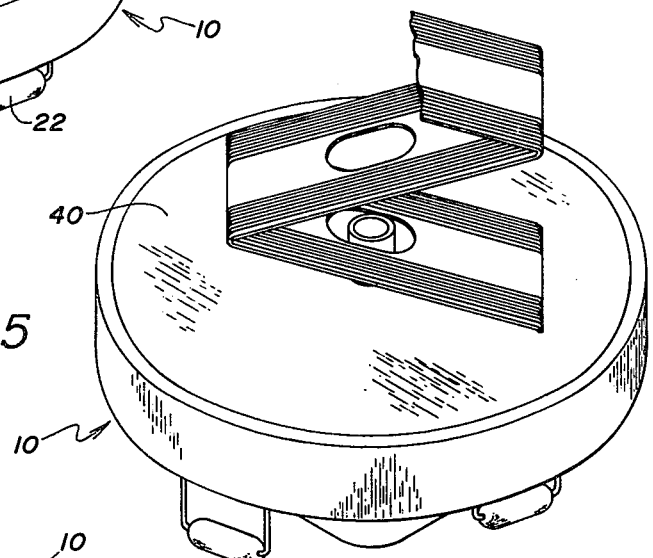
FIG. 5 is a perspective view of the member of FIG. 4 shown in final form for use as a sensing element.

FIG. 5 shows the sensing device 10 as assembled in FIG. 4 and further including an epoxy resin sealant 40 located over the top of surface 16. During construction of the device 10, a peripheral ridge 41 located around the surface 16 helps to confine the liquid epoxy mixture prior to its setting. Any suitable epoxy mixture may be used for the sealant covering 40. One such mixture is described below in reference to FIG. 7.

Figure 6:
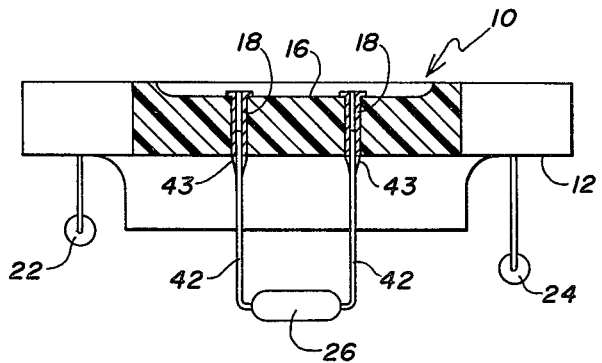
FIG. 6 is a partially sectioned view taken along view line 6—6 of FIG. 2 of the sensing device member as shown in FIG. 3.
Figure 7:
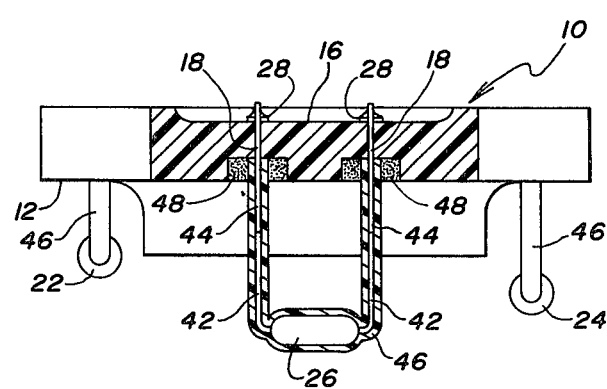
FIG. 7 is a partially sectioned view similar to FIG. 6 but showing a different version for the mounting of the sensing elements.

FIGS. 6 and 7 show partially sectional views of the sensing device member 10 having a plurality of sensing elements 22, 24 and 26 mounted thereon. The sections are taken along view lines 6—6 of FIG. 2 and show two different means for mounting the sensing element 26, either of which means may be used for the other elements 20, 22 and 24. In FIG. 6, the apertures 18 are shown as being plated through from the upper surface 16 to the lower mounting surface 12. By this means, the sensing element 26 is mounted to the member 10 and electrically connected by the soldering of its leads 42 at the points 43 which points are the lower extremities of the plated through apertures 18. The plating on the inside of apertures 18 is made as a part of the lands 28 located on the upper surface 16 and thus no further coupling is needed thereto. In FIG. 7, the apertures 18 are not plated through and thus the leads 42 must extend all the way therethrough in order to be connected to the lands 28. This connection may be made by any means such as soldering. In the case of sensing elements such as 26 which extend to some distance below the mounting surface 12, the leads 42 thereof must be extended. In this case, the extension is formed by a pair of electrical leads 44 which are butt-welded at their ends to the ends of leads 42. The leads 44 are made of nickel for their low thermal conductivity characteristics.

The sensing elements 22, 24 and 26 are shown encased in electrical insulation 46. The insulation or encasement 46 shown is commonly known as polyolefin shrink tubing and is available from Amp Incorporated under part No. 603342-1. The tubing used is clear in color and has a minimized thickness to reduce desensitizing effects on the sensing elements. In the present embodiment, tubing having a thickness of 0.015 inches (0.38 millimeters) or less is used. Generally, any form of electrically insulating plastic may be used. The polyolefin shrink tubing used for the present embodiment is readily commercially available and is easily applied to the present sensing elements.

The ends of the tubing extend into a pair of recesses 48 located in the bottom mounting surface 12 and are sealed thereto by an epoxy sealant contained within said recesses 48. Any suitable epoxy resin will suffice and the material used for the present embodiment is Isochem 401 NV clear with an aliphatic amine curing agent, Isochem 9/22 hardener, with a Thermoset 50Z black coloring in the ratio of 75%-22%-3%, respectively. These are available from Isochem Resins, Inc., of Lincoln, R. I. Thus mounted, the sensing element or diode is very well insulated from the environment in which it is located. Because the sensing device depends upon measurement of the current flowing through the various elements or diodes, it is important that leakage current between the leads 42 and 44 not be allowed to flow. Such leakage current would usually be caused by substances located in the liquid being monitored such as ground water minerals and the like. The combination of the shrink tubing surrounding the diode and the sealing of the ends thereof to the float or member 10 electrically isolate the diode from the liquid being monitored and thus block any such leakage current.

Thus, the present invention provides an improved sensing device which is insulated from adverse corrosive and electrical effects of the environment in which it operates. The improvement insures the long term operability and reliability of the sensing device.

The present disclosure is related in subject matter to two copending U.S. patent applications, SENSING DEVICE by Ralph A. Perry and Raymond J. Andrejasich, Ser. No. 197,955, and SENSING DEVICE by Ralph A. Perry, Ser. No. 197,953, both filed Oct. 17, 1980. The disclosures of these copending applications are hereby incorporated by reference herein. The present disclosure is further related to U.S. Pat. Nos. 4,221,125 and 4,223,552.

What is claimed is:

1. In a device for sensing a substance on the surface of a liquid of the type including a floatation means and a sensing element mounted on said floatation means for extending into said liquid, wherein the improvement comprises a plastic encasement enclosing all portions of said element to be exposed to said liquid for preventing interference with the operation of said element by substances in said liquid other than first said substance.

2. In the device of claim 1, wherein said sensing element is an axially leaded semiconductor junction device, said plastic encasement includes shrink tubing having a wall thickness of approximately 0.015 inches or less.

3. In the device of claim 2, wherein said sensing element has leads extending into said floatation means for mounting said sensing element thereto, the improvement further comprising epoxy resin material located for sealing said shrink tubing to said floatation means.

4. In the device of claim 3, wherein said floatation means includes a recess for containing said epoxy resin material.

5. In the device of claim 1, wherein said plastic encasement includes polyolefin shrink tubing.

* * * * *